(12) United States Patent
Du et al.

(10) Patent No.: US 9,867,532 B2
(45) Date of Patent: Jan. 16, 2018

(54) SYSTEM FOR DETECTING OPTICAL PARAMETER OF EYE, AND METHOD FOR DETECTING OPTICAL PARAMETER OF EYE

(71) Applicant: Beijing Zhigu Rui Tuo Tech Co., Ltd, Beijing (CN)

(72) Inventors: Lin Du, Beijing (CN); Hongjiang Zhang, Beijing (CN)

(73) Assignee: BEIJING ZHIGU RUI TUO TECH CO., LTD, Beijing (CN)

( * ) Notice: Subject to any disclaimer, the term of this patent is extended or adjusted under 35 U.S.C. 154(b) by 25 days.

(21) Appl. No.: 14/781,306

(22) PCT Filed: Dec. 4, 2013

(86) PCT No.: PCT/CN2013/088544
§ 371 (c)(1),
(2) Date: Sep. 30, 2015

(87) PCT Pub. No.: WO2015/014058
PCT Pub. Date: Feb. 5, 2015

(65) Prior Publication Data
US 2016/0135675 A1 May 19, 2016

(30) Foreign Application Priority Data
Jul. 31, 2013 (CN) .......................... 2013 1 0329797

(51) Int. Cl.
*A61B 3/12* (2006.01)
*A61B 3/00* (2006.01)
(Continued)

(52) U.S. Cl.
CPC .......... *A61B 3/0025* (2013.01); *A61B 3/0075* (2013.01); *A61B 3/113* (2013.01);
(Continued)

(58) Field of Classification Search
CPC .. A61B 3/12; A61B 3/14; A61B 3/102; A61B 3/0008; A61B 2090/3735
(Continued)

(56) References Cited

U.S. PATENT DOCUMENTS 4,264,154 A 4/1981 Petersen
4,572,616 A 2/1986 Kowel et al.
(Continued)

FOREIGN PATENT DOCUMENTS

CN 1372650 10/2002
CN 1470227 1/2004
(Continued)

OTHER PUBLICATIONS

International Search report dated Jun. 12, 2014 for PCT Application No. PCT/CN2013/088554, 4 pages.
(Continued)

*Primary Examiner* — Hung Dang
(74) *Attorney, Agent, or Firm* — Amin, Turocy & Watson, LLP

(57) ABSTRACT

An optical parameter of an eye is detected using an image collection apparatus that collects an image presented by a fundus. An imaging apparatus adjusts an imaging parameter of an optical path between an eye and the image collection apparatus, wherein the image collection apparatus obtains a clearest image that satisfies a defined clarity criterion or condition. An image processing apparatus processes the clearest image to obtain an optical parameter of the eye. The image of the fundus is captured, and an imaging parameter known in the optical path when the clearest image is captured is found, so that a direction currently being watched by the eye and a distance between the eye and a focusing point can be obtained through optical calculation. Consequently, a position of the focusing point of the eye can
(Continued)

be determined precisely for a wide range of concurrent applications for eye control interaction.

42 Claims, 8 Drawing Sheets

(51) Int. Cl.
    *A61B 3/113* (2006.01)
    *A61B 3/14* (2006.01)

(52) U.S. Cl.
    CPC .................. *A61B 3/12* (2013.01); *A61B 3/14* (2013.01); *A61B 2560/0223* (2013.01)

(58) Field of Classification Search
    USPC .......................... 351/206, 246, 208, 209, 210
    See application file for complete search history.

(56) References Cited

U.S. PATENT DOCUMENTS

| | | | |
|---|---|---|---|
| 5,182,585 | A | 1/1993 | Stoner |
| 5,537,163 | A | 7/1996 | Ueno |
| 6,072,443 | A | 6/2000 | Nasserbakht et al. |
| 6,111,597 | A | 8/2000 | Tabata |
| 6,151,061 | A | 11/2000 | Tokuhashi |
| 6,152,563 | A | 11/2000 | Hutchinson et al. |
| 6,325,513 | B1 | 12/2001 | Bergner et al. |
| 7,001,020 | B2 | 2/2006 | Yancey et al. |
| 7,298,414 | B2 | 11/2007 | Stavely et al. |
| 7,334,892 | B2 | 2/2008 | Goodall et al. |
| 7,486,988 | B2 | 2/2009 | Goodall et al. |
| 7,764,433 | B2 | 7/2010 | Kam et al. |
| 7,766,479 | B2 | 8/2010 | Ebisawa |
| 8,104,892 | B2 | 1/2012 | Hillis et al. |
| 8,109,632 | B2 | 2/2012 | Hillis et al. |
| 8,282,212 | B2 | 10/2012 | Hillis et al. |
| 8,384,999 | B1 | 2/2013 | Crosby et al. |
| 8,896,632 | B2 | 11/2014 | MacDougall et al. |
| 2002/0101568 | A1 | 8/2002 | Eberl et al. |
| 2002/0113943 | A1 | 8/2002 | Trajkovic et al. |
| 2003/0043303 | A1 | 3/2003 | Karuta et al. |
| 2003/0125638 | A1 | 7/2003 | Husar et al. |
| 2005/0003043 | A1 | 1/2005 | Sewal et al. |
| 2005/0014092 | A1 | 1/2005 | Hasegawa et al. |
| 2006/0016459 | A1 | 1/2006 | Mcfarlane et al. |
| 2006/0103808 | A1 | 5/2006 | Horie |
| 2006/0122530 | A1 | 6/2006 | Goodall et al. |
| 2006/0122531 | A1 | 6/2006 | Goodall et al. |
| 2006/0146281 | A1 | 7/2006 | Goodall et al. |
| 2006/0164593 | A1 | 7/2006 | Peyghambarian et al. |
| 2007/0019157 | A1 | 1/2007 | Hillis et al. |
| 2007/0211207 | A1 | 9/2007 | Lo et al. |
| 2008/0002262 | A1 | 1/2008 | Chirieleison |
| 2008/0106633 | A1 | 5/2008 | Blum et al. |
| 2009/0066915 | A1 | 3/2009 | Lai |
| 2009/0279046 | A1 | 11/2009 | Dreher et al. |
| 2009/0303212 | A1 | 12/2009 | Akutsu et al. |
| 2011/0018903 | A1 | 1/2011 | Lapstun et al. |
| 2011/0019258 | A1 | 1/2011 | Levola |
| 2011/0051087 | A1* | 3/2011 | Inoue ..................... A61B 3/12 351/206 |
| 2011/0213462 | A1 | 9/2011 | Holladay |
| 2011/0242277 | A1 | 10/2011 | Do et al. |
| 2011/0279277 | A1 | 11/2011 | Li-Chung |
| 2012/0013389 | A1 | 1/2012 | Thomas et al. |
| 2012/0092618 | A1 | 4/2012 | Yoo et al. |
| 2012/0113235 | A1 | 5/2012 | Shintani |
| 2012/0127422 | A1 | 5/2012 | Tian et al. |
| 2012/0133891 | A1 | 5/2012 | Jiang |
| 2012/0140044 | A1 | 6/2012 | Galstian et al. |
| 2012/0154277 | A1 | 6/2012 | Bar-Zeev et al. |
| 2012/0169730 | A1 | 7/2012 | Inoue |
| 2012/0206485 | A1 | 8/2012 | Osterhout et al. |
| 2012/0212499 | A1 | 8/2012 | Haddick et al. |
| 2012/0212508 | A1 | 8/2012 | Kimball |
| 2012/0242698 | A1 | 9/2012 | Haddick et al. |
| 2012/0290401 | A1 | 11/2012 | Neven |
| 2012/0307208 | A1 | 12/2012 | Trousdale |
| 2013/0044042 | A1 | 2/2013 | Olsson et al. |
| 2013/0050646 | A1 | 2/2013 | Nanbara |
| 2013/0072828 | A1 | 3/2013 | Sweis et al. |
| 2013/0107066 | A1 | 5/2013 | Venkatraman et al. |
| 2013/0127980 | A1 | 5/2013 | Haddick et al. |
| 2013/0135203 | A1 | 5/2013 | Croughwell, III |
| 2013/0147836 | A1 | 6/2013 | Small et al. |
| 2013/0241805 | A1 | 9/2013 | Gomez |
| 2013/0241927 | A1 | 9/2013 | Vardi |
| 2013/0278631 | A1 | 10/2013 | Border et al. |
| 2013/0335301 | A1 | 12/2013 | Wong et al. |
| 2013/0335404 | A1 | 12/2013 | Westerinen et al. |
| 2013/0342572 | A1 | 12/2013 | Poulos et al. |
| 2014/0078175 | A1 | 3/2014 | Forutanpour et al. |
| 2014/0160157 | A1 | 6/2014 | Poulos et al. |
| 2014/0225915 | A1 | 8/2014 | Theimer et al. |
| 2014/0225918 | A1 | 8/2014 | Mittal et al. |
| 2014/0232746 | A1 | 8/2014 | Ro et al. |
| 2014/0240351 | A1 | 8/2014 | Scavezze et al. |
| 2014/0267400 | A1 | 9/2014 | Mabbutt et al. |
| 2014/0267420 | A1 | 9/2014 | Schowengerdt et al. |
| 2014/0282224 | A1 | 9/2014 | Pedley |
| 2014/0375680 | A1 | 12/2014 | Ackerman et al. |
| 2015/0002542 | A1 | 1/2015 | Chan et al. |
| 2015/0035861 | A1 | 2/2015 | Salter et al. |
| 2015/0070391 | A1 | 3/2015 | Nishimaki et al. |
| 2015/0234184 | A1 | 8/2015 | Schowengerdt et al. |
| 2015/0235632 | A1 | 8/2015 | Liu et al. |
| 2016/0035139 | A1 | 2/2016 | Fuchs et al. |
| 2016/0171772 | A1 | 6/2016 | Ryznar et al. |
| 2016/0189432 | A1 | 6/2016 | Bar-Zeev et al. |
| 2016/0196603 | A1 | 7/2016 | Perez et al. |

FOREIGN PATENT DOCUMENTS

| | | |
|---|---|---|
| CN | 1141602 | 3/2004 |
| CN | 1527126 | 9/2004 |
| CN | 1604014 | 4/2005 |
| CN | 1645244 | 7/2005 |
| CN | 1653374 | 8/2005 |
| CN | 1901833 A | 1/2007 |
| CN | 1912672 | 2/2007 |
| CN | 2868183 | 2/2007 |
| CN | 1951314 A | 4/2007 |
| CN | 101069106 | 11/2007 |
| CN | 101072534 A | 11/2007 |
| CN | 101097293 | 1/2008 |
| CN | 101103902 A | 1/2008 |
| CN | 201005945 | 1/2008 |
| CN | 101116609 A | 2/2008 |
| CN | 101155258 | 4/2008 |
| CN | 101194198 | 6/2008 |
| CN | 101430429 | 5/2009 |
| CN | 201360319 | 9/2009 |
| CN | 201352278 | 11/2009 |
| CN | 101900927 | 1/2010 |
| CN | 101662696 | 3/2010 |
| CN | 201464738 | 5/2010 |
| CN | 101782685 | 7/2010 |
| CN | 101819331 | 9/2010 |
| CN | 101819334 | 9/2010 |
| CN | 201637953 | 11/2010 |
| CN | 101917638 | 12/2010 |
| CN | 201754203 | 3/2011 |
| CN | 102008288 | 4/2011 |
| CN | 102083390 | 6/2011 |
| CN | 102203850 | 9/2011 |
| CN | 102292017 A | 12/2011 |
| CN | 102419631 | 4/2012 |
| CN | 102481097 A | 5/2012 |
| CN | 101149254 | 6/2012 |
| CN | 102487393 | 6/2012 |
| CN | 202267785 | 6/2012 |
| CN | 102572483 | 7/2012 |
| CN | 102576154 | 7/2012 |

(56) References Cited

FOREIGN PATENT DOCUMENTS

| | | |
|---|---|---|
| CN | 202383380 | 8/2012 |
| CN | 102918444 | 2/2013 |
| CN | 102939557 | 2/2013 |
| CN | 102981270 | 3/2013 |
| CN | 103054695 | 4/2013 |
| CN | 103065605 | 4/2013 |
| CN | 103150013 | 6/2013 |
| CN | 103190883 A | 7/2013 |
| CN | 103197757 | 7/2013 |
| CN | 103280175 | 9/2013 |
| CN | 103297735 | 9/2013 |
| CN | 103353663 | 10/2013 |
| CN | 103353667 | 10/2013 |
| CN | 103353677 | 10/2013 |
| CN | 103558909 | 2/2014 |
| DE | 19959379 | 7/2000 |
| EP | 2646859 | 10/2013 |
| JP | 03023431 A | 1/1991 |
| JP | 2676870 B2 | 11/1997 |
| JP | H09289973 | 11/1997 |
| JP | 3383228 | 3/2003 |
| JP | 2003307466 | 10/2003 |
| JP | 2005058399 | 3/2005 |
| JP | 2007129587 | 5/2007 |
| JP | 201143876 | 3/2011 |
| JP | 2012199621 | 10/2012 |
| JP | 2012247449 | 12/2012 |
| TW | 201012448 | 4/2010 |
| WO | 2004023167 | 3/2004 |
| WO | 2005077258 | 8/2005 |
| WO | 2012075218 | 6/2012 |
| WO | 2012083415 | 6/2012 |
| WO | 2013074851 A1 | 5/2013 |

OTHER PUBLICATIONS

International Search Report dated Jan. 8, 2015 for PCT Application No. PCT/CN2014/088242, 2 pages.
Office Action dated Dec. 29, 2016 for U.S. Appl. No. 14/780,519, 25 pages.
Office Action dated Feb. 27, 2017 for U.S. Appl. No. 14/783,495, 39 pages.
Office Action dated Apr. 21, 2017 for U.S. Appl. No. 14/781,581, 19 pages.
Office Action dated Apr. 20, 2017 for U.S. Appl. No. 14/781,578, 77 pages.
Office Action dated Mar. 30, 2017 for U.S. Appl. No. 15/028,019, 36 pages.
International Search Report dated May 5, 2014 for PCT Application No. PCT/CN2013/088544, 4 pages.
International Search Report dated Mar. 6, 2014 for PCT Application No. PCT/CN2013/088540, 8 pages.
Jeong, et al. "Tunable microdoublet lens array", Optics Express, vol. 12, Issue 11, May 2004, pp. 2494-2500.
International Search Report dated Apr. 3, 2014 for PCT Application No. PCT/CN2013/088531, 10 pages.
International Search Report dated Feb. 27, 2014 for PCT Application No. PCT/CN2013/088522, 6 pages.
International Search Report dated May 8, 2014 for PCT Application No. PCT/CN2013/088547, 4 pages.
Kim et al., "A 200 s Processing Time Smart Image Sensor for an Eye Tracker using pixel-level analog image processing", IEEE Journal of Solid-State Circuits, vol. 44, No. 9, Sep. 2009, 10 pages.
Hansen et al., "In the eye of the beholder: a survey of models for eyes and gaze", IEEE Transactions on pattern analysis and machine intelligence, vol. 32, No. 3, Mar. 2010, 23 pages.
International Search Report dated May 28, 2014 for PCT Application No. PCT/CN2013/088553, 6 pages.
International Search Report dated May 28, 2014 for PCT Application No. PCT/CN2013/088545, 4 pages.
International Search Report dated Jun. 5, 2014 for PCT Application No. PCT/CN2013/088549, 4 pages.
Smith, et al., "Determining Driver Visual Attention With One Camera", IEEE Transactions on Intelligent Transportation Systems, vol. 4, No. 4, Dec. 2003, 14 Pages.
Singh, et al., "Human Eye Tracking and Related Issues: A Review", International Journal of Scientific and Research Publications, vol. 2, Issue 9, Sep. 2012, ISSN 2250-3153, 9 pages.
Ji et al., "Real-Time Eye, Gaze and Face Pose Tracking for Monitoring Driver Vigilance", Real-Time Imaging 8, 357-377 (2002) available online at http://www.idealibrary.com, 21 pages.
Office Action dated Jun. 29, 2017 for U.S. Appl. No. 14/783,495, 50 pages.
Office Action dated Jun. 29, 2017 for U.S. Appl. No. 14/783,503, 120 pages.
Gao et al. "Measuring Directionality of the Retinal Reflection with a Shack-Hartmann Wavefront Sensor", Dec. 2009, Optics Express, vol. 17, No. 25, Optical Society of America, 20 pages.
Office Action dated Jun. 8, 2017 for U.S. Appl. No. 14/779,968, 79 pages.
Office Action dated Jul. 12, 2017 for U.S. Appl. No. 14/780,519, 45 pages.
Office Action dated Oct. 4, 2017 for U.S. Appl. No. 14/781,584, 95 pages.
Office Action dated Nov. 9, 2017 for U.S. Appl. No. 14/781,578, 64 pages.
Office Action dated Nov. 9, 2017 for U.S. Appl. No. 14/780,519, 24 pages.

\* cited by examiner

SYSTEM FOR DETECTING OPTICAL PARAMETER OF EYE, AND METHOD FOR DETECTING OPTICAL PARAMETER OF EYE

RELATED APPLICATIONS

This application is a U.S. National Stage filing under 35 U.S.C. §371 of international patent cooperation treaty (PCT) application No. PCT/CN2013/088544, filed Dec. 4, 2013, and entitled "SYSTEM FOR DETECTING OPTICAL PARAMETER OF EYE, AND METHOD FOR DETECTING OPTICAL PARAMETER OF EYE," which claims priority to Chinese Patent Application No. 201310329797.5, filed with the Chinese Patent Office on Jul. 31, 2013 and entitled "SYSTEM AND METHOD FOR DETECTING OPTICAL PARAMETER OF EYE", which applications are hereby incorporated herein by reference in their respective entireties.

TECHNICAL FIELD

The subject disclosure relates to an optical system, and in particular, to detection an optical parameter of an eye.

BACKGROUND

With the development of technologies, there are more and more applications that control a device by detecting a natural action of a user, where applications that interact with the device by tracking an eye include the following applications.

The single lens reflex EOS 3 published by Canon has an exclusive eye control focusing function with 45 focusing points, which can automatically detect the motion of the pupil of the user eyeball that is watching the eyepiece of the camera. The eyeball is lighted by an infrared light emitting diode installed on the frame of the camera eyepiece, and the infrared light reflected back by the eyeball is cast onto an eye control BASIS (base stored image sensor). After the system detects the relative relationship between a position of the eyeball pupil and a calibration position, the camera identifies which focusing point in the focusing points is being watched by the user, so as to determine a sight line direction of the user, and perform automatic focusing on an object in the direction.

Tobii Technology develops an eye control interaction system, where an eye tracker (eye tracker) shoots and locates in real time a micro projection pattern reflected on the user eyeball (or directly shoots and locates the eyeball motion), so that the system can very precisely track a direction watched by the eye, to perform user eye control interaction or analyze a user reading behavior.

Google discloses, in U.S. Patent publication No. 2012/0290401, an apparatus and a method for determining a direction watched by an eye of a user through a wearable device, where the position of the user pupil is detected in real time by installing a camera or a CCD on a pair of glasses, so that the sight line direction of the user eye can be obtained.

As can be seen from the above, in the prior art, the sight line direction of the user is mainly obtained through the image on the eyeball surface. If the position of the focusing point of the eye is desired, the distance between the object and the eye is generally preset, as described in the foregoing eye control interaction technology, and the position of the focusing point can be obtained according to the sight line direction of the user and the set distance. In this case, if the distance between the object and the eye is not known, the position of the focusing point of the eye cannot be obtained. Alternatively, as disclosed in international patent publication No. WO2005077258A1, the position of the eye focusing point is obtained according to sight line directions of two eyes of the user and the intersection between the sight lines, so in this case, the sight line directions of the two eyes of the user need to be detected simultaneously, and the detection precision is not very high.

Medically, a fundus camera (Fundus Camera) is often used in ophthalmic diagnosis, where refined pictures of the fundus retina are captured to assist in diagnosis of some possible ophthalmic diseases, including determination of the eye diopter, as recorded in U.S. Pat. No. 7,001,020. However, the patent requires that the user stares at a specific target and has a test before an optical parameter of an eye can be determined. Therefore, the position of the focusing point of the eye in daily use cannot be determined.

SUMMARY

Various embodiments provide a system and a method for detecting an optical parameter of an eye, which are used to determine an optical parameter of an eye and particularly a position of a focusing point of the eye.

In a first aspect, a system is provided that detects an optical parameter of an eye, including an image collection apparatus configured to collect at least one image presented by a fundus of an eye, an imaging apparatus configured to adjust at least one imaging parameter of an optical path between the eye and the image collection apparatus, so that the image collection apparatus obtains a clearest image, and an image processing apparatus configured to process the image obtained by the image collection apparatus, to obtain at least one optical parameter of the eye when the image collection apparatus obtains the clearest image.

In a second aspect, a wearable optical device is provided, e.g., including the foregoing system for detecting an optical parameter of an eye.

In a third aspect, a method is provided for detecting an optical parameter of an eye, including collecting in real time at least one image presented by a fundus of an eye, adjusting at least one imaging parameter of an optical path between the eye and an image collection apparatus, so as to collect a clearest image, and processing the collected image, to obtain at least one optical parameter of the eye when the collected image is the clearest.

In one or more embodiments of the present application, the image of the fundus is captured, and an imaging parameter known in the optical path when the clearest image is captured is found, so that a direction which is currently being watched by the eye and a distance between the eye and a focusing point can be obtained through optical calculation, and a position of the focusing point of the eye can further be determined precisely, providing a further application basis for an eye control interaction related technology at the same time.

BRIEF DESCRIPTION OF THE DRAWINGS

The various embodiments of the subject application will become more fully understood from the detailed description given herein below for illustration only, and thus are not limiting, and wherein.

DETAILED DESCRIPTION

The various embodiments are described in detail in the following with reference to accompanying drawings and embodiments.

Figure 1:
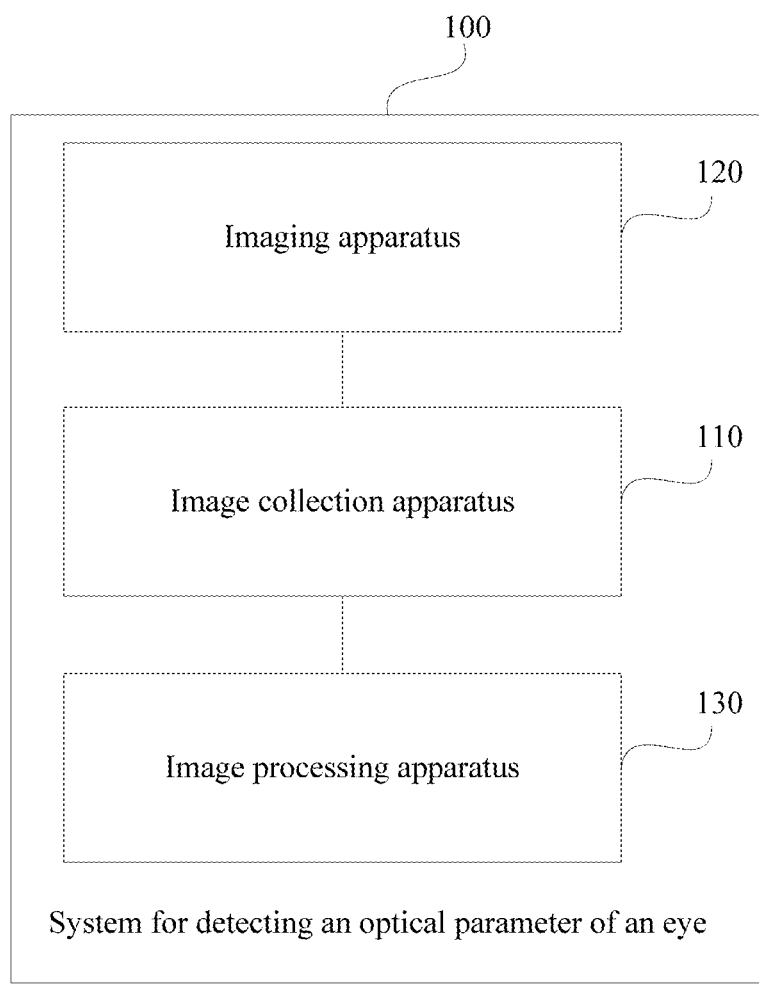
FIG. 1 is a structural block diagram of a system for detecting an optical parameter of an eye according to an embodiment.

As shown in FIG. 1, an embodiment provides a system 100 for detecting an optical parameter of an eye, including an image collection apparatus 110 configured to collect an image presented by a fundus, an imaging apparatus 120 configured to adjust an imaging parameter between an eye and the image collection apparatus 110, so that the image collection apparatus 110 obtains a clearest image, and an image processing apparatus 130 configured to process the image obtained by the image collection apparatus 110, to obtain an optical parameter of the eye when the image collection apparatus obtains the clearest image.

In an embodiment, the optical parameter of the eye when the image collection apparatus obtains the clearest image is obtained by analyzing and processing the image of the eye fundus, so that a position of a current focusing point of the eye can be obtained through calculation, providing a basis for further implementing an eye self-adaptive operation.

Herein, the image presented by the "fundus" is mainly an image presented on a retina, which may be an image of the fundus, or an image of another object cast to the fundus. The eye herein may be a human eye or an eye of another animal.

Figure 2:
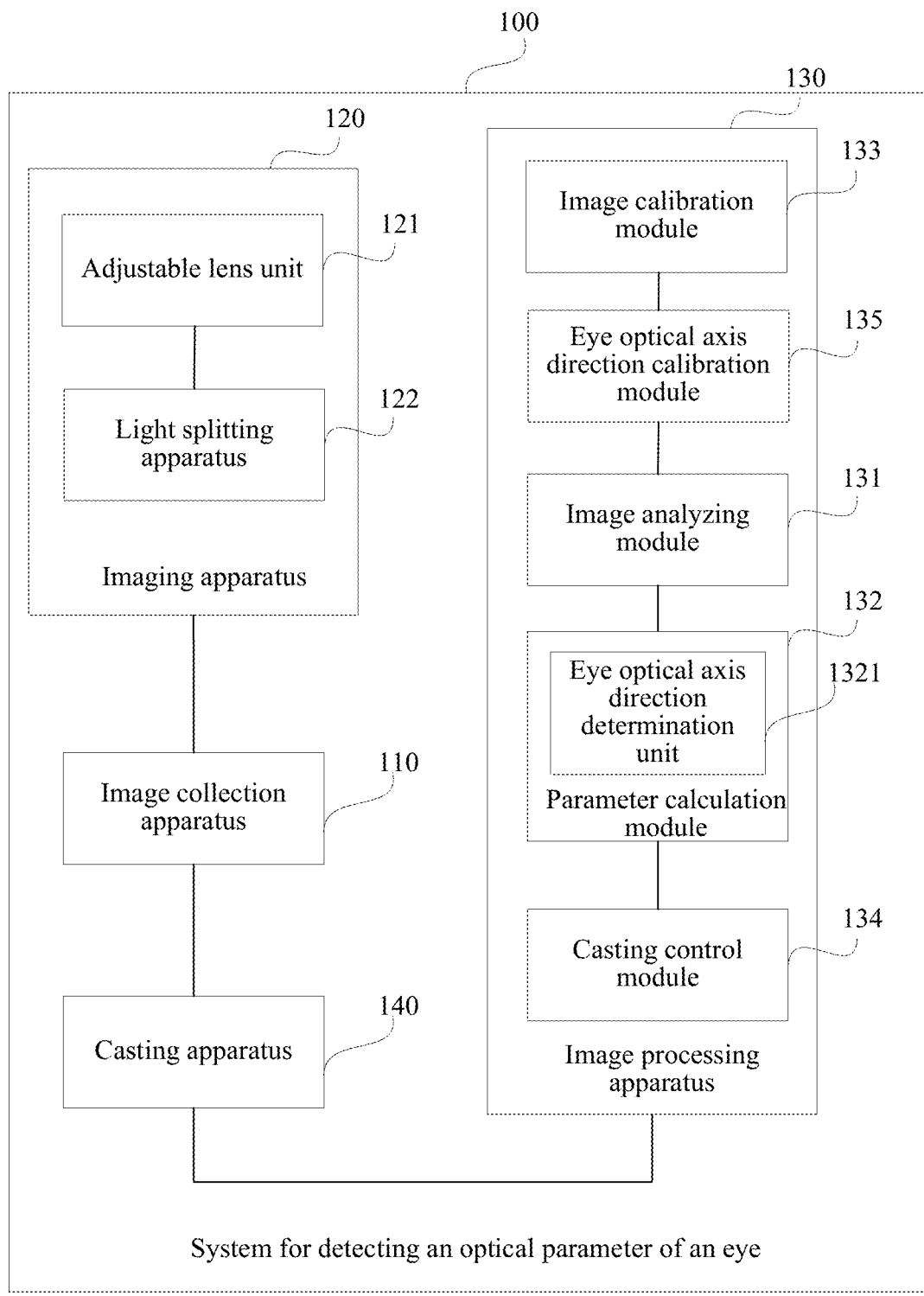
FIG. 2 is a structural block diagram of another system for detecting an optical parameter of an eye according to an embodiment.

As shown in FIG. 2, in a possible implementation manner of the embodiment, the image collection apparatus 110 is a micro camera. In another possible implementation manner of the embodiment, the image collection apparatus 110 may also use a photosensitive imaging device directly, such as a CCD or a CMOS.

In a possible implementation manner of the embodiment, the imaging apparatus 120 includes: an adjustable lens unit 121, located in the optical path between the eye and the image collection apparatus 110, where a focal length of the adjustable lens unit 121 is adjustable and/or a position of the adjustable lens unit 121 in the optical path is adjustable. Through the adjustable lens unit 121, a system equivalent focal length from the eye to the image collection apparatus 110 is adjustable. Through adjustment of the adjustable lens unit 121, the image collection apparatus 110 obtains the clearest image of the fundus when the adjustable lens unit 121 is located at a certain position or is in a certain state. In this implementation manner, the adjustable lens unit 121 is adjusted continuously and in real time during detection.

In a possible implementation manner of the embodiment, the adjustable lens unit 121 is a focal length adjustable lens, configured to adjust a focal length thereof by adjusting a refractive index and/or shape thereof, which is specifically: 1) the focal length is adjusted by adjusting a curvature of at least one surface of the focal length adjustable lens, for example, adjusting the curvature of the focal length adjustable lens by increasing or reducing the quantity of a liquid medium in a cavity formed by two layers of transparent layers; and 2) the focal length is adjusted by changing the refractive index of the focal length adjustable lens, for example, the focal length adjustable lens is filled with a specific liquid crystal medium, and the voltage of an electrode corresponding to the liquid crystal medium is adjusted to adjust an arrangement manner of the liquid crystal medium, so as to change the refractive index of the focal length adjustable lens.

In another possible implementation manner of the embodiment, the adjustable lens unit 121 includes a lens set, configured to adjust a relative position between lenses in the lens set, to adjust a focal length of the lens set.

Besides the foregoing two manners where the optical path parameter of the system is changed by adjusting the feature of the adjustable lens unit 121, the optical path parameter of the system may also be changed by adjusting the position of the adjustable lens unit 121 in the optical path.

In a possible implementation manner of the embodiment, in order not to affect the viewing experience of the user on a viewed object, and in order to enable the system to be portably applied to a wearable device, the imaging apparatus 120 further includes: a light splitting apparatus 122, configured to form a light transferring path between the eye and the viewed object, and a light transferring path between the eye and the image collection apparatus 110. In this way, the optical path can be folded, thereby reducing the volume of the system while not affecting other experience of the user as much as possible.

In this implementation manner, the light splitting apparatus includes a first light splitting unit, located between the eye and the viewed object, and configured to transmit light from the viewed object to the eye, and transfer light from the eye to the image collection apparatus.

The first light splitting unit may be a beam splitter, a light splitting optical waveguide (including optical fiber), or another proper light splitting device.

In a possible implementation manner of the embodiment, the image processing apparatus 130 includes an optical path calibration module, configured to calibrate the optical path of the system, for example, align and calibrate an optical axis of the optical path, so as to ensure the detection precision.

In a possible implementation manner of the embodiment, the image processing apparatus 130 includes an image analyzing module 131 configured to analyze the image obtained by the image collection apparatus, to find the clearest image, and a parameter calculation module 132 configured to calculate the optical parameter of the eye according to the clearest image and the imaging parameter known by the system when the clearest image is obtained.

In this implementation manner, through the imaging apparatus 120, the image collection apparatus 110 can obtain the clearest image, but the clearest image needs to be found through the image analyzing module 131. In this case, the optical parameter of the eye can be obtained through calculation according to the clearest image and the optical path parameter known by the system. Herein, the optical parameter of the eye may include an optical axis direction of the eye.

In a possible implementation manner of the embodiment, the system further includes a casting apparatus 140 configured to cast a light spot to the fundus. In a possible implementation manner, a function of the casting apparatus may be implemented by a micro projector.

The cast light spot herein may not have a specific pattern and be only used to lighten the fundus.

Figure 3A:
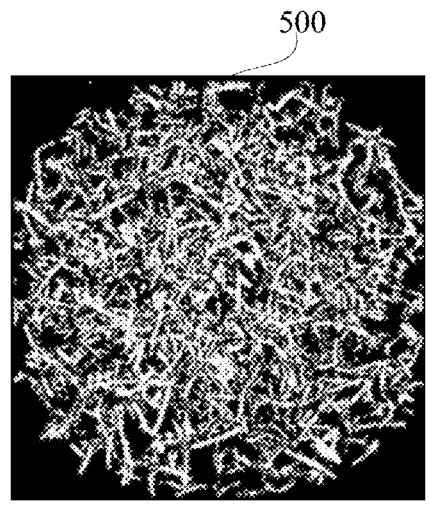
FIG. 3a is a schematic diagram of a light spot pattern used in a system for detecting an optical parameter of an eye according to an embodiment.
Figure 3B:
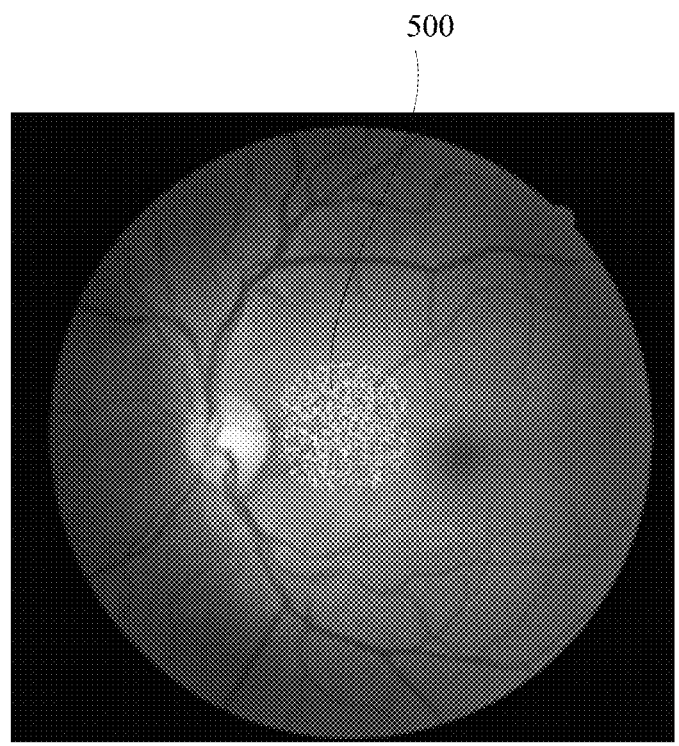
FIG. 3b is a schematic diagram of a fundus image with a light spot pattern captured by a system for detecting an optical parameter of an eye according to an embodiment.

In a preferable implementation manner of the embodiment, the cast light spot includes a pattern rich in features. The pattern is rich in features, which can facilitate detection and improve the detection precision. FIG. 3a is a schematic diagram of a light spot pattern 500. The pattern may be generated by a light spot pattern generator, such as frosted glass. FIG. 3b shows an image of the fundus captured when the light spot pattern 500 is cast.

In order not to affect the eye in viewing an object normally, the light spot is an infrared light spot invisible to the eye.

In this case, to reduce interference from another optical spectrum an emergent surface of the casting apparatus may be provided with an eye invisible light transmission filter, for example, an infrared transmission filter, and an incident surface of the image collection apparatus is provided with an eye invisible light transmission filter.

In a possible implementation manner of the embodiment, the image processing apparatus 130 further includes a casting control module 134 configured to control, according to a result obtained by the image analyzing module, brightness of the light spot cast by the casting apparatus.

For example, the casting control module 134 may self-adaptively adjust the brightness according to the feature of the image obtained by the image collection apparatus 110. Herein, the feature of the image includes an image feature contrast, a texture feature, and so on.

Herein, a special case of controlling the brightness of the light spot cast by the casting apparatus 140 is: turning on or off the casting apparatus 140. For example, when the user keeps watching a certain point, the casting apparatus may be turned off periodically; when the fundus of the user is bright enough, the casting apparatus 140 may be turned off, and only fundus information is used to detect a distance from a focusing point of a current sight line of the eye to the eye.

Besides, the casting control module 134 may further control, according to environment light, the brightness of the light spot cast by the casting apparatus.

In a possible implementation manner of the embodiment, the image processing apparatus 130 further includes an image calibration module 133 configured to calibrate the image of the fundus to obtain at least one reference image corresponding to the image presented by the fundus.

The image analyzing module 131 performs comparison calculation for the image obtained by the image collection apparatus 130 and the reference image, to obtain the clearest image. Herein, the clearest image may be an obtained image least different from the reference image. In this implementation manner, the difference between the currently obtained image and the reference image is calculated through an existing image processing algorithm, for example, using a classic phase difference automatic focusing algorithm.

In a possible implementation manner of the embodiment, the parameter calculation module 132 includes an eye optical axis direction determination unit 1321 configured to obtain an eye optical axis direction according to a feature of the eye when the clearest image is obtained.

Herein, the feature of the eye may be obtained from the clearest image or obtained elsewhere. The eye optical axis direction indicates a direction watched by the sight line of the eye.

In a possible implementation manner of the embodiment, the eye optical axis direction determination unit 1321 includes a first determination subunit, configured to obtain the eye optical axis direction according to a feature of the fundus when the clearest image is obtained. Compared with the manner of obtaining the eye optical axis direction through features of the pupil and eyeball surface, the manner of determining the eye optical axis direction through the feature of the fundus is higher in precision.

When the light spot pattern is cast to the fundus, the size of the light spot pattern may be greater or smaller than that of a visible region of the fundus, where, when the area of the light spot pattern is smaller than or equal to that of the visible region of the fundus, the eye optical axis direction may be determined by using a classic feature point matching algorithm (for example, a scale invariant feature transform (SIFT) algorithm) to detect a position of the light spot pattern on the image relative to the fundus.

Further, when the area of the light spot pattern is greater than or equal to that of the visible region of the fundus, the eye optical axis direction may be determined through a position of the obtained light spot pattern on the image relative to an original light spot pattern (obtained by the image calibration module), to determine the sight line direction of the user.

In another possible implementation manner of the embodiment, the eye optical axis direction determination unit 1321 includes a second determination subunit, configured to obtain the eye optical axis direction according to a feature of the pupil of the eye when the clearest image is obtained. Herein, the feature of the eye pupil may be obtained from the clearest image or obtained elsewhere. The manner of obtaining the eye optical axis direction through the feature of the eye pupil belongs to the prior art, which is not detailed herein again.

In a possible implementation manner of the embodiment, the image processing apparatus 130 further includes an eye optical axis direction calibration module 135, configured to calibrate the eye optical axis direction, so that the eye optical axis direction is determined more precisely.

In this implementation manner, the imaging parameter known by the system includes: a constant imaging parameter and a real-time imaging parameter, where the real-time imaging parameter is adjustable parameter information of the adjustable lens unit when the clearest image is obtained, and the parameter information may be obtained through real-time record when the clearest image is obtained.

Figure 4A:
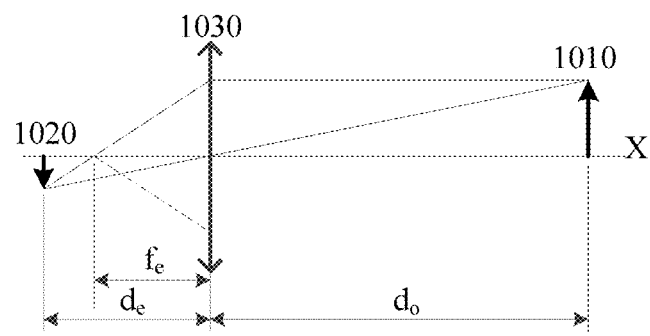
FIG. 4a is a schematic diagram of an optical path for eye imaging according to an embodiment.

After the current optical parameter of the eye is obtained, the distance from the eye focusing point to the eye can be obtained through a calculation, e.g., as follows:

FIG. 4a is a schematic diagram of eye imaging. With reference to a lens imaging formula in the classic optical theory, the following formula (1) may be obtained according to FIG. 4a:

$$\frac{1}{d_o} + \frac{1}{d_e} = \frac{1}{f_e} \quad (1)$$

where $d_o$ represents a distance from a current viewed object 1010 of the eye to an eye equivalent lens 1030, $d_e$ represents a distance from a real image 1020 on the retina to the eye equivalent lens 1030, $f_e$ represents an equivalent focal length of the eye equivalent lens 1030, and X represents the sight line direction of the eye (which may be obtained according to the optical axis direction of the eye).

Figure 4B:
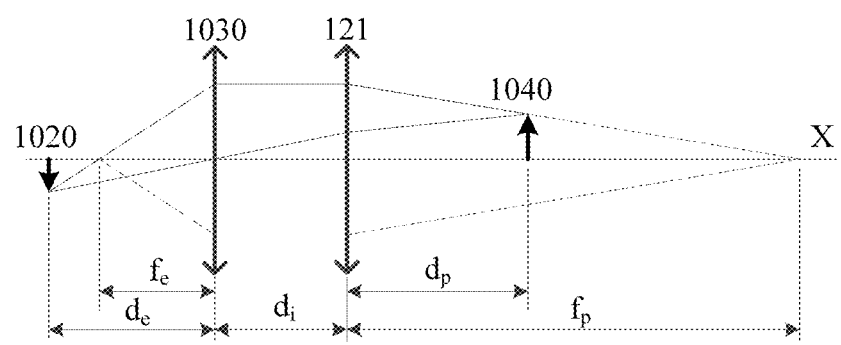
FIG. 4b is a schematic diagram of a distance from an eye focusing point to an eye and obtained according to an imaging parameter known by a system and an optical parameter of the eye according to an embodiment.

FIG. 4b is a schematic diagram of a distance from the eye focusing point to the eye and obtained according to the optical parameter known by the system and the optical parameter of the eye. A light spot 1040 in FIG. 4b forms a virtual image (not shown in FIG. 4b) through the adjustable lens unit 121. Assuming that a distance from the virtual image to the lens is x (not shown in FIG. 4b), the following equation set may be obtained with reference to formula (1):

$$\begin{cases} \frac{1}{d_p} - \frac{1}{x} = \frac{1}{f_p} \\ \frac{1}{d_i + x} + \frac{1}{d_e} = \frac{1}{f_e} \end{cases} \quad (2)$$

where $d_p$ represents an optical equivalent distance from the light spot 1040 to the adjustable lens unit 121, $d_i$ represents an optical equivalent distance from the adjustable lens unit 121 to the eye equivalent lens 1030, $f_p$ represents a value of the focal length of the adjustable lens unit 121, and $d_i$ represents a distance from the eye equivalent lens 1030 to the adjustable lens unit 121.

The distance $d_o$ from the current viewed object 1010 (the eye focusing point) to the eye equivalent lens 1030 can be obtained according to (1) and (2), as shown in formula (3):

$$d_o = d_i + \frac{d_p \cdot f_p}{f_p - d_p} \quad (3)$$

Because the distance from the viewed object 1010 to the eye is obtained according to the foregoing calculation, and the eye optical axis direction can be obtained through the previous record, the position of the eye focusing point can be obtained easily, which provides a basis for subsequent further eye related interaction.

Figure 5:
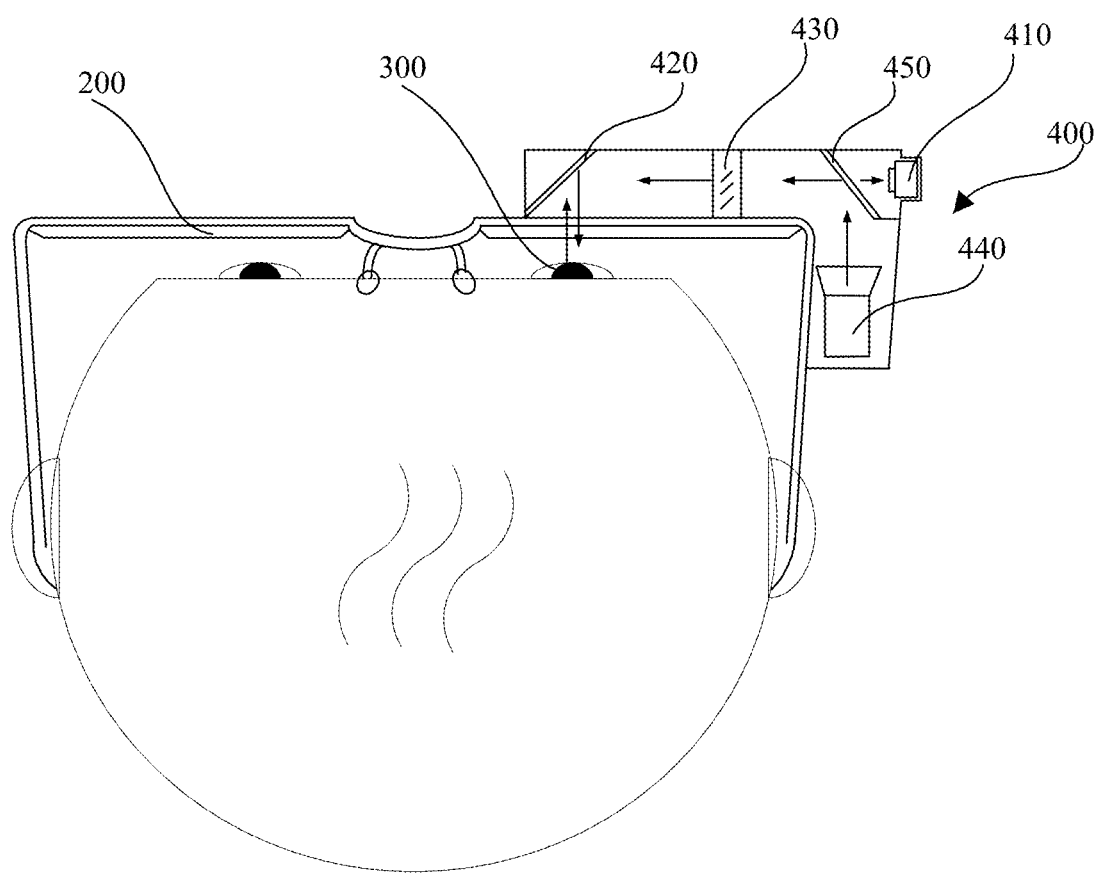
FIG. 5 is a schematic diagram of an application of a system for detecting an optical parameter of an eye on a pair of glasses according to an embodiment.

FIG. 5 shows an embodiment where a system 400 for detecting an eye focusing point is applied to a pair of glasses 200 in a possible implementation manner of an embodiment, which includes the content recorded in the implementation manner shown in FIG. 2. Specifically, as can be seen from FIG. 5, in this implementation manner, the system 400 of this implementation manner is integrated on the right side (not limited thereto) of the glasses 200, which includes a micro camera 410, which functions in the same way as the image collection apparatus recorded in the implementation manner of FIG. 2, and is arranged on the right outside of the glasses 200, so as not to affect the sight line of the user in viewing the object normally.

The glasses 200 can include a first beam splitter 420, which functions in the same way as the first light splitting unit recorded in the implementation manner of FIG. 2, and is arranged with a certain tilt angle at the intersection between a direction watched by an eye 300 and an incident direction of the camera 410, and transmits light of the viewed object entering the eye 300 and reflects light from the eye to the camera 410.

Further, an focal length adjustable lens 430 can be included, which functions in the same way as the focal length adjustable lens recorded in the implementation manner of FIG. 2, and is located between the first beam splitter 420 and the camera 410, and adjusts the value of the focal length in real time, so that the camera 410 can capture a clearest image of the fundus when the focal length is set to a certain value.

In this implementation manner, no image processing apparatus is shown in FIG. 5, which functions in the same way as the image processing apparatus shown in FIG. 2.

Generally, the fundus is not bright enough, and therefore, it would be best to increase light to the fundus. In this implementation manner, the fundus is lighted by a light emitting source 440. In order not to affect the user experience, the light emitting source 440 herein is a light source emitting light invisible to the eye, which is a near-infrared light emitting source that affects the eye 300 slightly and to which the camera 410 is sensitive.

In this implementation manner, because the light emitting source 440 is located on the right outside of the frame of the glasses, a second beam splitter 450 is required to transfer, to the fundus together with the first beam splitter 420, the light emitted by the light emitting source 440. In this implementation manner, because the second beam splitter 450 is located before the incident surface of the camera 410, it is further required to transmit the light from the fundus to the second beam splitter 450.

As can be seen, in this implementation manner, to improve the user experience and the collection definition of the camera 410, the first beam splitter 420 may have features such as a high infrared reflectance and a high visible light transmittance. For example, the foregoing features may be achieved by arranging an infrared reflective film on a side of the first beam splitter 420 towards the eye 300.

As can be seen from FIG. 5, in this implementation manner, because the system 400 for detecting an eye focusing point is located on a side of a lens of the glasses 200 far away from the eye 300, when the optical parameter of the eye is calculated, the lens may also be considered as a part of the eye. In this case, it is not required to know the optical feature of the lens.

In another implementation manner of the embodiment, the system 400 for detecting an eye focusing point may be located on a side of a lens of the glasses 200 close to the eye 300. In this case, the optical feature parameter of the lens needs to be obtained in advance, and the influence factor of the lens is considered when the distance between the eye and the focusing point is calculated.

The light emitted by the light emitting source is reflected by the second beam splitter 420, cast by the focal length adjustable lens 430, and reflected by the first beam splitter 420, then enters the eye of the user through the lens of the glasses 200, and finally reaches the retina of the fundus. The camera 410 captures the image of the fundus through an optical path formed by the first beam splitter 420, the focal length adjustable lens 430, and the second beam splitter 450 through the pupil of the eye 300.

Figure 6:
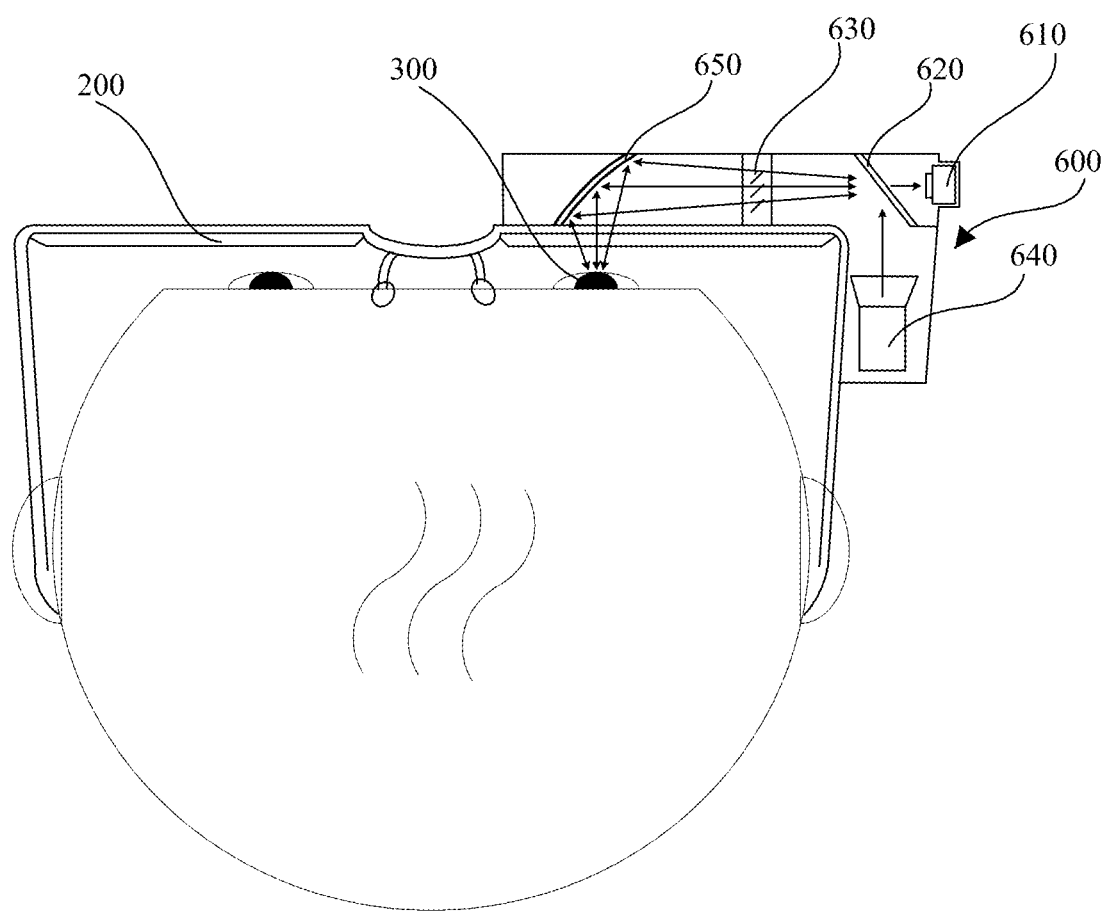
FIG. 6 is a schematic diagram of an application of another system for detecting an optical parameter of an eye on a pair of glasses according to an embodiment.

FIG. 6 is a schematic structural diagram of a system 600 for detecting an eye focusing point in another implementation manner of the embodiment. As can be seen from FIG. 6, this implementation manner is similar to that shown in FIG. 5 in that, the system includes a micro camera 610, a second beam splitter 620, and a focal length adjustable lens 630, and different from that shown in FIG. 5 in that, in this implementation manner, a casting apparatus 640 is a casting apparatus 640 casting a light spot pattern, and the first beam splitter in the implementation manner of FIG. 5 is replaced with a curved beam splitter 650.

Herein, the curved beam splitter 650 transfers, to an image collection apparatus, images presented by a fundus and separately corresponding to positions of a pupil in the case of different eye optical axis directions. In this way, the camera can capture images formed by blending and superimposing images of the eyeball from different angles. However, only the fundus part of the pupil can be imaged clearly on the camera, while other parts fail to be clearly imaged due to out of focus. Therefore, the imaging of the fundus part is not affected seriously, and the feature of the fundus part can still be detected. Therefore, compared with the implementation manner of FIG. 5, in this implementation manner, an image of the fundus can be obtained very well even though the eye watches an object in different directions, so that the application range of the system for detecting eye focusing point of this implementation manner is wider, and the detection precision thereof is higher.

Figure 7:
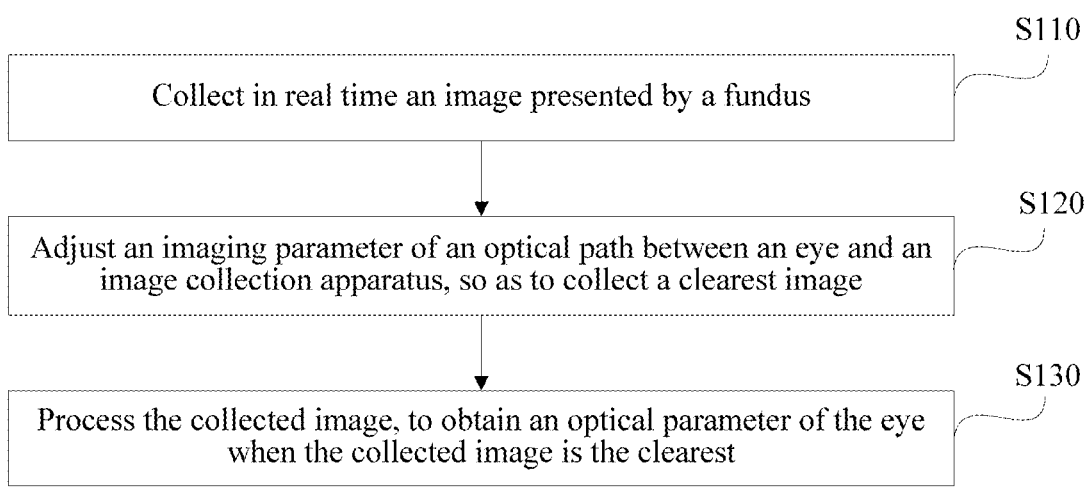
FIG. 7 is a flowchart of a method for detecting an optical parameter of an eye according to an embodiment.

FIG. 7 shows a method for detecting an optical parameter of an eye according to an embodiment, including the following operations.

S110: Collect in real time an image presented by a fundus.

S120: Adjust an imaging parameter of an optical path between an eye and an image collection apparatus, so as to collect a clearest image.

S130: Process the collected image, to obtain an optical parameter of the eye when the collected image is the clearest.

In a possible implementation manner of the embodiment, the method further includes operation S140: obtaining a position of a focusing point of the eye according to the optical parameter of the eye.

In a possible implementation manner of the embodiment, before the operation S130: processing the collected image, the method further includes calibrating the image of the fundus, to obtain at least one reference image corresponding to the image presented by the fundus.

Figure 8:
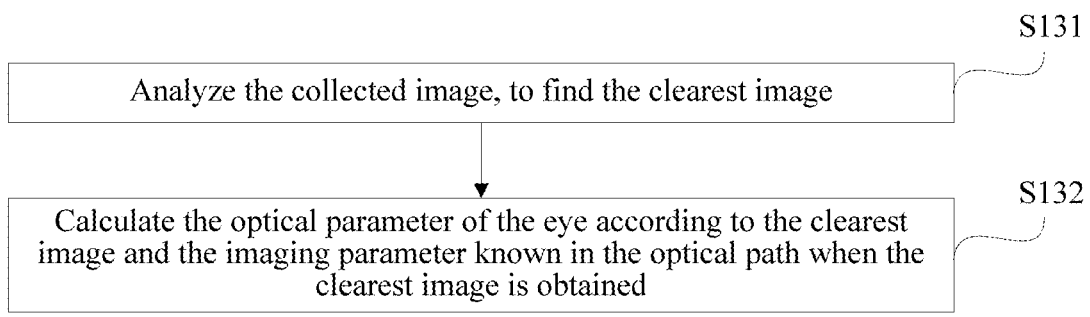
FIG. 8 is a flowchart of step S130 of a method for detecting an optical parameter of an eye according to an embodiment.

As shown in FIG. 8, a possible implementation manner of the embodiment, the operation S130: processing the collected image, to obtain an optical parameter of the eye when the collected image is the clearest includes the following operations.

S131: Analyze the collected image, to find the clearest image.

S132: Calculate the optical parameter of the eye according to the clearest image and the imaging parameter known in the optical path when the clearest image is obtained.

In a possible implementation manner of the embodiment, the operation S131 includes performing comparison calculation for the collected image and the reference image, to obtain the clearest image.

In a possible implementation manner of the embodiment, the operation S132 includes obtaining an eye optical axis direction according to a feature of the eye when the clearest image is obtained.

In a possible implementation manner of the embodiment, the operation of obtaining an eye optical axis direction according to a feature of the eye when the clearest image is obtained includes obtaining an eye optical axis direction according to a feature of the fundus when the clearest image is obtained.

In another possible implementation manner of the embodiment, the operation of obtaining an eye optical axis direction according to a feature of the eye when the clearest image is obtained includes obtaining an eye optical axis direction according to a feature of a pupil of the eye when the clearest image is obtained.

In a possible implementation manner of the embodiment, before the operation of obtaining an eye optical axis direction according to a feature of the eye when the clearest image is obtained, the method further includes an operation of calibrating the eye optical axis direction.

In a possible implementation manner of the embodiment, in operation S120, the imaging parameter of the optical path between the eye and the image collection apparatus is adjusted in a manner of adjusting a focal length of a lens unit in the optical path between the eye and the image collection apparatus and/or a position of the lens unit in the optical path.

In a possible implementation manner of the embodiment, the operation of collecting in real time an image presented by a fundus includes collecting images presented by the fundus and separately corresponding to positions of the pupil in the case of different eye optical axis directions.

In a possible implementation manner of the embodiment, the method further includes an operation of casting a light spot to the fundus.

The cast light spot includes a pattern rich in features and is an infrared light spot.

To reduce the influence of visible light on the detection precision, this implementation manner, the light spot cast to the fundus is filtered by an eye invisible light transmission filter; and the collected image is filtered by the eye invisible light transmission filter. For example, a near-infrared transmission light filter may be used, so that only near-infrared light can pass through the light filter.

In a possible implementation manner of the embodiment, the method further includes an operation of: controlling brightness of the cast light spot according to a result obtained by analyzing the collected image.

The method of the embodiment may be implemented through the apparatus embodiment in FIG. 1 to FIG. 6. For the specific implementation means, refer to the description of the apparatus embodiment. Details are not described herein again.

A person skilled in the art may understand that, in the method of the specific implementation manner, the sequence numbers of the steps or operations do not mean an execution order, the execution order of the steps or operations should be determined according to their functions and internal logic, and shall not be construed as any limitation to the implementation process of the specific implementation manner.

Figure 9:
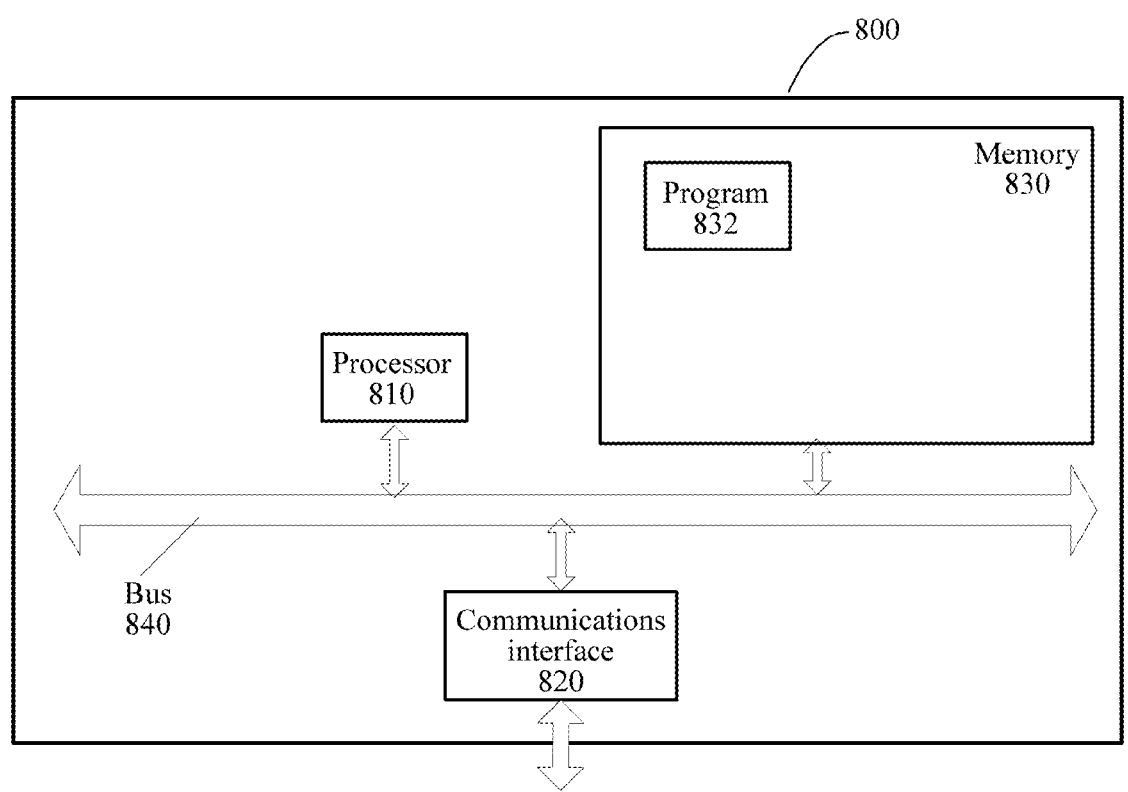
FIG. 9 is a structural block diagram of an image processing apparatus of a system for detecting an optical parameter of an eye according to an embodiment.

FIG. 9 is a schematic structural diagram of an image processing apparatus 800 in a system for detecting an optical parameter of an eye provided in an embodiment, and the specific implementation of the image processing apparatus 800 is not limited in the specific embodiment. As shown in FIG. 9, the image processing apparatus 800 may include a processor (processor) 810, a communications interface (Communications Interface) 820, a memory (memory) 830, and a communication bus 840.

The processor 810, the communications interface 820, and the memory 830 communicate with each other through the communication bus 840.

The communications interface 820 is configured to communicate with a network element such as a client.

The processor 810 is configured to execute a program 832, and may specifically execute related operations in the method embodiment shown in FIG. 8.

Specifically, the program 832 may include a program code, where the program code includes a computer operation instruction.

The processor 810 may be a central processing unit CPU, or an application specific integrated circuit (ASIC), or be configured as one or more integrated circuits for implementing the embodiments.

The memory 830 is configured to store the program 832. The memory 830 may include a high-speed RAM memory, and may further include a non-volatile memory, for example, at least one disk memory. The program 832 may specifically enable the image processing apparatus 800 to execute the following operations analyzing the image obtained by the image collection apparatus, to find the clearest image, and calculating the optical parameter of the eye according to the clearest image and the imaging parameter known by the system when the clearest image is obtained.

For the specific implementation of the operations in the program 832, reference may be made to corresponding descriptions about corresponding operations and units in the foregoing embodiments, and details are not described herein again. It may be clearly understood by a person skilled in the art that, for the purpose of convenient and brief description, for the specific working processes of the foregoing devices and modules, reference may be made to the description about the corresponding process in the foregoing method embodiment, and the details are not described herein again.

An embodiment further provides a wearable optical device. The wearable optical device may be the frame glasses shown in FIG. 5 or FIG. 6, or a contact lens. The wearable optical device includes the system for detecting an optical parameter of an eye recorded in the foregoing embodiments.

In another possible implementation manner of the embodiment, the system for detecting an optical parameter of an eye may also be applied to another eye related device, for example, a non-wearable optical device such as a telescope; or the system for detecting an optical parameter may be further applied to another imaging and receiving apparatus, such as a camera, except the eye.

A person of ordinary skill in the art may be aware that, in combination with the examples described in the embodiments disclosed in this specification, units and method operations may be implemented by electronic hardware, or a combination of computer software and electronic hardware. Whether the functions are performed by hardware or software depends on particular applications and design constraint conditions of the technical solutions. A person skilled in the art may use different methods to implement the described functions for each particular application, but it should not be considered that the implementation goes beyond the scope.

When the functions are implemented in a form of a software functional unit and sold or used as an independent product, the functions may be stored in a computer-readable storage medium. Based on such an understanding, the various embodiments essentially, or the part contributing to the prior art, or a part of the technical solutions may be implemented in a form of a software product. The computer software product can be stored in a storage medium, and includes several instructions for instructing a computer device (which may be a personal computer, a server, or a network device) to perform all or a part of the operations of the methods described in the embodiments. The foregoing storage medium includes: any medium that can store program codes, such as a USB flash drive, a removable hard disk, a read-only memory (ROM), a random access memory (RAM), a magnetic disk, or an optical disc.

The foregoing implementation manners are merely intended for describing the present invention rather than limiting the present invention. A person of ordinary skill in the art should understand that modifications and variations may still be made without departing from the spirit and scope. Therefore, all equivalent technical solutions shall fall within the scope, and the patent protection scope various embodiments shall be subject to the claims.

What is claimed is:

1. A system, comprising:
   an image collection apparatus configured to collect at least one image presented by a fundus of an eye;
   an imaging apparatus configured to adjust at least one imaging parameter of an optical path between the eye and the image collection apparatus, wherein the image collection apparatus obtains an image of the at least one image that satisfies at least a defined clarity criterion; and
   an image processing apparatus configured to process the image to obtain at least one optical parameter of the eye in response to the image collection apparatus obtaining the image that satisfies at least the defined clarity criterion, wherein the image processing apparatus comprises a parameter calculation module configured to determine the at least one optical parameter of the eye according to the image that satisfies the at least the defined clarity criterion and the at least one imaging parameter corresponding to a time when the image that satisfies the at least the defined clarity criterion was obtained.

2. The system according to claim 1, wherein the image processing apparatus further comprises:
   an image analyzing module configured to analyze the at least one image collected by the image collection apparatus to find a clearest image of the at least one image relative to the defined clarity criterion; wherein the parameter calculation module is configured to determine the at least one optical parameter of the eye according to the clearest image and the at least one imaging parameter corresponding to a time when the clearest image was obtained.

3. The system according to claim 2, wherein the image processing apparatus further comprises:
   an image calibration module configured to obtain at least one reference image corresponding to the at least one image presented by the fundus.

4. The system according to claim 3, wherein the image analyzing module is further configured to compare the at least one image collected by the image collection apparatus and the at least one reference image to obtain the clearest image.

5. The system according to claim 2, wherein the parameter calculation module is further configured to obtain a position of a focusing point of the eye according to the at least one optical parameter of the eye.

6. The system according to claim 2, wherein the parameter calculation module comprises:
an eye optical axis direction determination unit configured to obtain an eye optical axis direction according to a feature of the eye in response to the clearest image being obtained.

7. The system according to claim 6, wherein the eye optical axis direction determination unit comprises:
a first determination subunit configured to obtain the eye optical axis direction according to a feature of the fundus in response to the clearest image being obtained.

8. The system according to claim 6, wherein the eye optical axis direction determination unit comprises:
a second determination subunit configured to obtain the eye optical axis direction according to a feature of a pupil of the eye in response to the clearest image being obtained.

9. The system according to claim 6, wherein the image processing apparatus further comprises:
an eye optical axis direction calibration module configured to calibrate the eye optical axis direction.

10. The system according to claim 2, further comprising:
a casting apparatus configured to cast a light spot to the fundus.

11. The system according to claim 10, wherein the light spot cast by the casting apparatus comprises a pattern.

12. The system according to claim 10, wherein the casting apparatus is an infrared light spot casting apparatus.

13. The system according to claim 12, wherein an emergent surface of the casting apparatus is provided with an eye invisible light transmission filter.

14. The system according to claim 12, wherein an incident surface of the image collection apparatus is provided with an eye invisible light transmission filter.

15. The system according to claim 10, wherein the image processing apparatus further comprises:
a casting control module configured to control, according to a result obtained by the image analyzing module, a brightness of the light spot cast by the casting apparatus.

16. The system according to claim 1, wherein the imaging apparatus comprises:
an adjustable lens unit, located in the optical path between the eye and the image collection apparatus, wherein a focal length of the adjustable lens unit is adjustable or a position of the adjustable lens unit in the optical path is adjustable.

17. The system according to claim 16, wherein the adjustable lens unit comprises:
a focal length adjustable lens, having the focal length or alternatively having a different focal length, configured to adjust the focal length or alternatively the different focal length by adjusting a refractive index and/or shape of the focal length adjustable lens.

18. The system according to claim 16, wherein the adjustable lens unit comprises:
a lens set configured to adjust a relative position between at least two lenses in the lens set to adjust another focal length of the lens set.

19. The system according to claim 1, wherein the imaging apparatus further comprises:
a light splitting apparatus configured to form a first light transferring path between the eye and a viewed object, and a second light transferring path between the eye and the image collection apparatus.

20. The system according to claim 19, wherein the light splitting apparatus comprises:
a first light splitting unit, located between the eye and the viewed object, and configured to transmit light from the viewed object to the eye, and transfer light from the eye to the image collection apparatus.

21. The system according to claim 20, wherein the first light splitting unit is a beam splitter or a light splitting optical waveguide.

22. The system according to claim 21, wherein the first light splitting unit is a curved beam splitter configured to transfer, to the image collection apparatus, the at least one image presented by the fundus, and wherein the at least one image respectively correspond to at least one position of a pupil associated with different eye optical axis directions.

23. The system according to claim 1, wherein the system is a wearable optical device comprising the image collection apparatus, the imaging apparatus, and the image processing apparatus.

24. A method, comprising:
collecting at least one image presented by a fundus of an eye;
adjusting at least one imaging parameter of an optical path between the eye and an image collection apparatus to collect an image of the at least one image that at least satisfies a defined clarity condition; and
processing the image to obtain at least one optical parameter of the eye in response to the image being determined to satisfy the defined clarity condition, wherein the processing the image to obtain the at least one optical parameter of the eye comprises calculating the at least one optical parameter of the eye according to the image that satisfies the defined clarity condition and the at least one imaging parameter known from the optical path in response to the image that satisfies the defined clarity condition being obtained.

25. The method according to claim 24, wherein the processing the image to obtain the at least one optical parameter of the eye further comprises:
analyzing the at least one image to find a clearest image; and
calculating the at least one optical parameter of the eye according to the clearest image and the at least one imaging parameter known in the optical path in response to the clearest image being obtained.

26. The method according to claim 25, further comprising:
before the processing of the image, calibrating the at least one image of the fundus to obtain at least one reference image corresponding to the at least one image presented by the fundus.

27. The method according to claim 26, wherein the analyzing the at least one image to find the clearest image comprises:
comparing the at least one image and the at least one reference image to obtain the clearest image.

28. The method according to claim 25, further comprising:
obtaining a position of a focusing point of the eye according to the at least one optical parameter of the eye.

29. The method according to claim 25, wherein the calculating the at least one optical parameter of the eye according to the clearest image and the at least one imaging parameter known in the optical path in response to the clearest image being obtained comprises:

obtaining an eye optical axis direction according to a feature of the eye in response to the clearest image being obtained.

30. The method according to claim 29, further comprising:

calibrating the eye optical axis direction before the eye optical axis direction is obtained according to the feature of the eye.

31. The method according to claim 25, wherein the calculating the at least one optical parameter of the eye according to the clearest image and the at least one imaging parameter known in the optical path in response to the clearest image being obtained comprises:

obtaining the eye optical axis direction according to a feature of the fundus in response the clearest image being obtained.

32. The method according to claim 25, wherein the calculating the at least one optical parameter of the eye according to the clearest image and the at least one imaging parameter known in the optical path in response to the clearest image being obtained comprises:

obtaining the eye optical axis direction according to a feature of a pupil of the eye in response to the clearest image being obtained.

33. The method according to claim 25, further comprising:

casting a light spot to the fundus.

34. The method according to claim 33, wherein the light spot comprises a defined pattern.

35. The method according to claim 33, wherein the light spot is an infrared light spot.

36. The method according to claim 35, wherein the light spot cast to the fundus is directed through a filter that blocks visible light transmission.

37. The method according to claim 35, wherein the at least one image is filtered by an eye invisible light transmission filter.

38. The method according to claim 33, further comprising:

controlling a brightness of the light spot according to a result obtained by analyzing the at least one image.

39. The method according to claim 24, wherein the at least one imaging parameter of the optical path between the eye and the image collection apparatus is adjusted in a manner of adjusting a focal length of a lens unit in the optical path between the eye and the image collection apparatus or a position of the lens unit in the optical path.

40. The method according to claim 24, wherein the collecting the at least one image presented by the fundus comprises:

collecting images presented by the fundus that respectively correspond to positions of a pupil associated with different eye optical axis directions.

41. A computer readable storage device comprising executable instructions that, in response to execution, cause a wearable optical apparatus comprising a processor to perform operations, comprising:

receiving at least one image of a fundus of an eye;

determining an image of the at least one image that at least satisfies a defined clarity characteristic, wherein the determining comprises modifying at least one imaging parameter of an optical path between the eye and an image collection apparatus; and processing the image to obtain at least one optical parameter of the eye in response to the image being determined to satisfy the defined clarity characteristic, wherein the processing the image to obtain the at least one optical parameter of the eye comprises determining the at least one optical parameter of the eye based on information represented by the image that satisfies the defined clarity characteristic and the at least one imaging parameter of the optical path in response to the image that satisfies the defined clarity characteristic being determined.

42. The computer readable storage device according to claim 41, wherein the processing the image to obtain the at least one optical parameter of the eye further comprises:

analyzing the at least one image to determine a clearest image; and determining the at least one optical parameter of the eye based on information represented by the clearest image and the at least one imaging parameter of the optical path in response to the clearest image being determined.

* * * * *